United States Patent
Sato (10) Patent No.: US 8,808,672 B2
(45) Date of Patent: Aug. 19, 2014

(54) LIQUID COSMETIC

(75) Inventor: Hiroshi Sato, Fujioka (JP)

(73) Assignee: Mitsubishi Pencil Company, Limited, Shinagawa-ku, Tokyo (JP)

(*) Notice: Subject to any disclaimer, the term of this patent is extended or adjusted under 35 U.S.C. 154(b) by 0 days.

(21) Appl. No.: 14/000,558

(22) PCT Filed: Apr. 26, 2012

(86) PCT No.: PCT/JP2012/061179
§ 371 (c)(1),
(2), (4) Date: Aug. 20, 2013

(87) PCT Pub. No.: WO2012/147835
PCT Pub. Date: Nov. 1, 2012

(65) Prior Publication Data
US 2013/0330288 A1    Dec. 12, 2013

(30) Foreign Application Priority Data

Apr. 28, 2011 (JP) ................... 2011-102081

(51) Int. Cl.
| | |
|---|---|
| *A61K 8/19* | (2006.01) |
| *A61K 8/29* | (2006.01) |
| *A61Q 1/10* | (2006.01) |
| *A61K 8/81* | (2006.01) |
| *A61K 8/85* | (2006.01) |

(52) U.S. Cl.
CPC ... *A61K 8/85* (2013.01); *A61K 8/29* (2013.01); *A61Q 1/10* (2013.01); *A61K 8/8164* (2013.01); *A61K 8/8152* (2013.01); *A61K 8/8182* (2013.01)
USPC ......................................................... 424/63

(58) Field of Classification Search
None
See application file for complete search history.

(56) References Cited

U.S. PATENT DOCUMENTS

| | | | |
|---|---|---|---|
| 6,488,945 | B2 | 12/2002 | Sato |
| 7,205,271 | B2 | 4/2007 | Drzewinski et al. |
| 2002/0051756 | A1 | 5/2002 | Sato |
| 2006/0084586 | A1 | 4/2006 | Drzewinski et al. |
| 2007/0202064 | A1 | 8/2007 | Drzewinski et al. |
| 2009/0060849 | A1 | 3/2009 | Song et al. |
| 2009/0175813 | A1* | 7/2009 | Morita et al. ............ 424/63 |

FOREIGN PATENT DOCUMENTS

| | | |
|---|---|---|
| JP | 2000-247833 A | 9/2000 |
| JP | 2005-053809 A | 3/2005 |
| JP | 2008-031057 A | 2/2008 |

(Continued)

OTHER PUBLICATIONS

International Search Report (PCT/ISA/210) issued on Jul. 3, 2012, by the Japanese Patent Office as the International Searching Authority for International Application No. PCT/EP2012/061179.

*Primary Examiner* — Anand Desai
*Assistant Examiner* — Melissa Mercier
(74) *Attorney, Agent, or Firm* — Buchanan Ingersoll & Rooney PC (57) ABSTRACT

To provide a liquid cosmetic which is loaded into a liquid applicator having an applying part and suitably used as a cosmetic for eye-makeup around the eyes, the liquid cosmetic comprises, at least, 1 to 20% by mass of high-brightness particles, 2 to 10% by mass of film-forming resin, 0.3% by mass or more of an anionic polymer compound having a thickening effect, and water, and is configured such that the viscosity at 25° C. and a shear rate of 76.8 s$^{-1}$ in an EMD type viscometer falls within the range of 250 to 1,000 mPa·s.

5 Claims, 5 Drawing Sheets

(56) References Cited

FOREIGN PATENT DOCUMENTS

| | | |
|---|---|---|
| JP | 2008-516950 A | 5/2008 |
| JP | 2009-029721 A | 2/2009 |
| JP | 2010-222332 A | 10/2010 |
| JP | 2010-235489 A | 10/2010 |
| JP | 2010-538038 A | 12/2010 |
| WO | WO 2007/083753 A1 | 7/2007 |
| WO | WO 2007/123115 A1 | 11/2007 |

* cited by examiner

LIQUID COSMETIC

TECHNICAL FIELD

The present invention relates to a liquid cosmetic, more detailedly relating to a liquid cosmetic that is excellent in water resistance and abrasion resistance. The liquid cosmetic can be smoothly ejected without causing precipitation of high-brightness particles presenting brilliant colors and without clogging up in the conduit of the applicator part, and is suitable for eyeliner and other cosmetics.

BACKGROUND ART

In recent years, in order to enhance fashionability, eyeliner cosmetics have come to use coloring materials of various colors and coloring materials including high-brightness particles of large sizes.

However, the coloring material of large particle sizes clogs up in the liquid ejection path when a container for holding the liquid cosmetic therein is used, causing difficulties in smooth ejection. Further, since the coloring material precipitates, it has been necessary to provide a stirring ball or stirring bar for stirring up the precipitated coloring material.

For this reason, in order to provide a liquid cosmetic excellent in water resistance and skin adhesion, the applicants hereof have proposed a liquid cosmetic comprising an inorganic pigment, a particular dispersing agent and a particular film-forming agent (e.g., see Patent Document 1) and a water-based liquid makeup cosmetic comprising a dispersing agent, a film-forming agent, a surfactant and water, which is a liquid cosmetic made of a flake pigment, a pigment dispersing agent and water, and optionally added with a surfactant as necessary in order to provide a water-based liquid makeup cosmetic that enables easy drawing of fine lines, is excellent in waterproof sticking performance and can be homogeneously redispersed by lightly shaking (e.g., see Patent Document 2).

These liquid cosmetics have been excellent so far, but are purposed to different subjects and different physical properties of the composition from those of the present invention, so that these are distinguished. Under such circumstances, the consumers who purchase eye makeup cosmetics and the like, earnestly want a liquid cosmetic that is excellent in usability without the need of any stirring work and has such an excellent dischargability as to enable smooth ejection of high brightness coloring materials having large particle sizes without any clogging of the liquid in the liquid ejection path.

Further, in order to provide an aqueous liquid cosmetic including pearl pigments, which is excellent in settling durative stability, can be readily redispersed by stirring even if pigments are precipitated and is suitable for a liquid cosmetic applicator with a brush as an applying part for storing an aqueous cosmetic fluid, the applicants hereof have also proposed a liquid cosmetic that is formed of, at least, a surfactant, an alkyl acrylate copolymer emulsion, a pearl pigment, anionic polymer compound as a structural viscosity providing agent and presents a particular viscosity falling within a range at a predetermined shear rate with a particular non-Newtonian viscosity index (n) (see Patent Document 3).

However, as compared with the above Patent Document 3, the composition of the present invention includes no surfactant and no alkyl acrylate copolymer emulsion and does not need any re-dispersion process because pigment precipitation is eliminated by blending a particular anionic polymer compound. Accordingly, the above liquid cosmetic is different from the present invention in subjects and physical properties and can be distinguished.

On the other hand, Patent Document 4 discloses a makeup cosmetic including a particular acrylate crosspolymer. This makeup cosmetic is an oil-in-water type emulsion, which includes hydrophobically treated porous silica as an essential component and provides performance excellent in water-repellency, cosmetic coating durability, excessive sebum absorbency and stability. However, the disclosure is different from the present invention in subjects, physical properties of composition and others, and can be distinguished.

Patent Document 5 discloses a rheology modifier/hair styling resin as a cross-linked linear poly(vinyl amide/polymerizable carboxylic acid) copolymer and its production process and a hair-care prescription for providing long-lasting curl-retention for users. However, this disclosure is different from the present invention in subjects, physical properties of composition and others, and can be distinguished.

RELATED ART DOCUMENTS

Patent Documents

Patent Document 1: International Publication WO2007/083753 (claims, examples, and others)
Patent Document 2: International Publication WO2007/123115 (claims, examples, and others)
Patent Document 3: Japanese Patent Application Laid-open 2000-247833 (claims, examples, and others)
Patent Document 4: Japanese Patent Application Laid-open 2010-222332 (claims, examples, and others)
Patent Document 5: Japanese Patent Application Disclosure 2008-516950 (claims, examples, and others)

SUMMARY OF THE INVENTION

Problems to be Solved by the Invention

In view of the problems of the above related art and the status quo, in order to solve the problems, it is an object of the present invention to provide a liquid cosmetic which is excellent in water resistance and abrasion resistance, and can be adhered closely to the skin without letting the ejected high-brightness particles come off in flakes. That is, the liquid cosmetic can be smoothly ejected without causing a clogging of large particle sizes of high brightness coloring materials to exert a glittering effect around eyes in the liquid ejection flow passage and the precipitation is prevented by increasing the liquid viscosity without any loss of ejection performance, when used in a container for the liquid cosmetic.

Means for Solving the Problems

In order to solve the above prior art and other problems, the inventors hereof earnestly investigated to provide a liquid cosmetic that can be suitably used as a cosmetic to be held in a container. Resultantly, the inventors succeeded in finding that blending of an anionic polymer compound having a specific thickening effect in a specific amount can provide a cosmetic that can be smoothly ejected without causing clogging of high-brightness particles. Furthermore, the cosmetic is presented an increased liquid viscosity without any loss of ejection performance to prevent the precipitation, is excellent in water resistance and abrasion resistance and can be adhered closely to the skin without letting the ejected high-brightness particles come off in flakes. Thus, the present inventors have completed the invention.

That is, the present invention resides in the following (1) to (5):—

(1) A liquid cosmetic comprising, at least, 1 to 20% by mass of high-brightness particles, 2 to 10% by mass of film-forming resin, 0.3 to 2% by mass of an anionic polymer compound having a thickening effect, and water, wherein the viscosity at 25° C. and a shear rate of 76.8 s$^{-1}$ in an EMD type viscometer falls within the range of 250 to 1,000 mPa·s.

(2) The liquid cosmetic described in (1), wherein the anionic polymer compound having a thickening effect is at least one selected from a group consisting of methylvinyl ether/maleic acid crosspolymer, acrylates/acrylate ester of alkyl having 10 to 30 carbon atoms crosspolymer, and acrylic acid/vinylpyrrolidone crosspolymer.

(3) The liquid cosmetic described in (1) or (2), wherein the cosmetic is used as an eye makeup cosmetic.

(4) The liquid cosmetic described in any one of (1) to (3), wherein the color of the vehicle (base) is transparent.

(5) The liquid cosmetic described in any one of (1) to (4), wherein the cosmetic is stored in a liquid applicator having an applying part.

Effect of the Invention

According to the present invention, it is possible to provide a liquid cosmetic which can be smoothly ejected without causing clogging in the liquid ejection path even if a high brightness coloring material of large particle sizes is used in order to produce glittering effect around eyes. Furthermore, the liquid cosmetic can be prevented from precipitation by increasing the liquid viscosity without any loss of ejection performance, is excellent in water resistance and abrasion resistance, and can be adhered closely to the skin without letting the ejected high-brightness particles come off in flakes.

BRIEF DESCRIPTION OF DRAWINGS

FIG. 2 is an illustrative diagram of an applying part of the liquid applicator of FIG. 1, (a) a plan view of the applying part and (b) a sectional view of the applying part.

FIG. 3 (a) is a partial sectional illustrative diagram of the applicator bent by 2 mm, setting the tip of the applying face as a start point, (b) and (c) plan and sectional views showing in detail the shape and structure of the applying part.

MODES FOR CARRYING OUT THE INVENTION

Hereinafter, the embodiment of the present invention will be described in detail.

The liquid cosmetic contains, at least, 1 to 20% by mass of high-brightness particles, 2 to 10% by mass of film-forming resin, 0.3 to 2% by mass of an anionic polymer compound having a thickening effect, and water, wherein the viscosity at 25° C. and a shear rate of 76.8 s$^{-1}$ in an EMD type viscometer falls within the range of 250 to 1,000 mPa·s.

The high-brightness particles used in the present invention are not particularly limited, and any stuff can be used as long as it is usually used for cosmetics. For example, at least, one selected from mica-titanium, metal-coated mica-titanium, metal-coated glass powder, metal oxide-coated glass powder, metal oxide-coated synthetic phlogopite, argentine, bismuth oxychloride, polyethylene terephthalate.aluminum.epoxy laminate powder, polyethylene terephthalate.polyolefin laminate film powder, and polyethylene terephthalate.polymethyl methacrylate laminate film powder, can be used.

Among them, use of metal oxide-coated glass powder or polyethylene terephthalate.polymethyl methacrylate laminate film powder is preferable because more vivid and excellent colors can be obtained.

The particle size of the high-brightness particles being used is preferably 50 to 500 μm or more preferably 150 to 300 μm. If the particle size is less than 50 μm, the effect of large high-brightness particles is insufficient. On the other hand, the particle size exceeding 500 μm is not preferable since granular feeling will occur.

"Particle size" in the present invention (inclusive of examples) is a value determined based on the mean particle diameter of measurement results by observing arbitrary particles of 20 or more with a microscope.

The content of these high-brightness particles is preferably 1 to 20% by mass (which will be merely referred to hereinbelow as "%") or more preferably 2 to 10% relative to the total amount of the liquid cosmetic.

If the content of the high-brightness particles is less than 1%, the effect of large high-brightness particles is insufficient. On the other hand, if the content exceeds 20%, the ejection flow passage will clog up since the solid content is too much.

In the present invention, other coloring materials may be used in combination with the high-brightness particles. As the coloring materials, at least, one inorganic pigment, selected from black iron oxides, yellow iron oxides, chromium oxide, ultramarine, Prussian blue, zinc oxide, aluminum oxide, silica, titanium oxide, magnesium oxide, chromium hydroxide, calcium carbonate, magnesium carbonate, titanium yellow, and red ochre, can be used.

The contents of these inorganic pigments are not particularly limited. Arbitrary amounts of inorganic pigments may be used as long as the viscosity of the cosmetic satisfies the specification of the present invention. Other than the high-brightness particles and inorganic pigments, organic pigments, various kinds of dyes and carbon black may be used if required.

As examples of the anionic polymer compound having a thickening effect used in the present invention, one or two kinds of crosspolymers selected from methylvinyl ether/maleic acid crosspolymer, acrylates/acrylate ester of alkyl having 10 to 30 carbon atoms crosspolymer, and acrylic acid/vinylpyrrolidone crosspolymer are preferably used.

These methylvinyl ether/maleic acid crosspolymer, acrylates/acrylate ester of alkyl having 10 to 30 carbon atoms crosspolymer, and acrylic acid/vinylpyrrolidone crosspolymer have a nature of increasing viscosity by alkaline neutralization.

The basic structure of methylvinyl ether/maleic acid crosspolymer is a micro-gel polymer formed by evenly crosslinked copolymers of methylvinyl ether and maleic anhydride with decadiene. Acrylates/acrylate ester of alkyl having 10 to 30 carbon atoms crosspolymer is a networked copolymer composed of, at least, one first monomer unit selected from acrylic acid and methacrylic acid and at least, one second monomer unit selected from acrylate esters of alkyl having 10 to 30 carbon atoms, and methacrylate esters of alkyl having 10 to 30 carbon atoms. Further, acrylic acid/vinylpyrrolidone crosspolymer is a copolymer of acrylic acid and vinylpyrrolidone.

The alkali as a neutralizer is not particularly limited, but alkanolamines such as triethanolamine and aminomethyl propanol, ammonia, potassium hydroxide, and sodium hydroxide can be listed.

In view of application performance, or the capability of homogeneous application without application unevenness, use of methylvinyl ether/maleic acid crosspolymer and acrylates/acrylate ester of alkyl having 10 to 30 carbon atoms crosspolymer is preferable.

As the commercially available products, the "STABILEZE" series (manufactured by ISP Japan Inc.) and the "Carbopol" series (manufactured by Lubrizol Corporation) can be mentioned.

The content of the anionic polymer compound having thickening effect is preferably 0.3 to 2%, more preferably 0.4 to 1%, relative to the total amount of the liquid cosmetic.

If the content is less than 0.3%, precipitation of the coloring material takes place. On the other hand, the content exceeding 2% is not preferable since the viscosity becomes too viscous, exhibiting poor applying performance.

As the film-forming resin used in the present invention, homopolymer or copolymer, made up of one or more kinds of compounds selected from acrylic acid, methacrylic acid or ester of alkyl, having 1 to 4, and 8 carbon atoms, for such acids, is used. Preferably, the homopolymer or copolymer is acrylic resin or alkyl acrylate copolymer having acidic residues as side chains in its repeating unit and can dissolve into water by neutralization. As particularly preferable alkyl acrylate copolymers, a copolymer compound consisting of tert-butyl acrylate, ethyl acrylate and methacrylic acid can be exemplified. As a commercially available product, Luvimer 100P (manufactured by BASF SE) can be mentioned.

The content of these film-forming resins is preferably 2 to 10%, more preferably 3 to 6%, relative to the total amount of the liquid cosmetic. If the content is less than 2%, the cosmetic presents insufficiency in water resistance and abrasion resistance. On the other hand, the content exceeding 10% is not economic since no additional improvement is achieved.

The liquid cosmetic of the present invention contains the aforementioned high-brightness particles, film-forming resin and an anionic polymer compound having a thickening effect, and further includes additives such as chelating agents, pH modifiers, moisturizing agents, thickener, and preservatives, the remaining part being balanced with water such as purified water and deionized water.

In the present invention, in terms of precipitation control and redispersibility of the high-brightness particles and applying performance, the viscosity of the liquid cosmetic (the viscosity measured by an EMD type viscometer at 25° C. using a standard cone rotor with a speed of 20 rpm at a shear rate of 76.8 $s^{-1}$) is specified to fall within the range of 250 to 1,000 mPa·s. Preferably the viscosity falls within a range from 280 to 900 mPa·s.

The viscosity less than 250 mPa·s is not preferable since precipitation of the coloring material takes place. On the other hand, the viscosity exceeding 1,000 mPa·s is too viscous, degrading applying performance.

More preferably, the viscosities at a shear rate of 3.83 $s^{-1}$, 19.20 $s^{-1}$ and 38.3 $s^{-1}$ fall within the following ranges: —
3.83 $s^{-1}$: 2,500 to 10,000 mPa·s, preferably 3,500 to 9,000 mPa·s;
19.20 $s^{-1}$: 1,000 to 3,000 mPa·s, preferably 1,100 to 2,500 mPa·s; and,
38.30 $s^{-1}$: 500 to 1,500 mPa·s, preferably 600 to 1,300 mPa·s.

Adjustment of the viscosity within the above range can be made by achieving appropriate combination of the contents of the high-brightness particles, film-forming resin, anionic polymer compound having a thickening effect and water, and by adding such as a thickener.

Since the liquid cosmetic of the present invention is given as an aqueous composition without emulsion, the vehicle (base) color is transparent. Therefore, the cosmetic is excellent in design performance and suitable for eye makeup cosmetics for eyeliner around the eyes and eyebrows.

In thus composed liquid cosmetic of the present invention containing, at least, 1 to 20% of high-brightness particles, 2 to 10% of film-forming resin, 0.3 to 2% of an anionic polymer compound having a thickening effect, and water, the viscosity at 25° C. and a shear rate of 76.8 $s^{-1}$ in an EMD type viscometer is specified to fall within the range of 250 to 1,000 mPa·s, whereby it is possible to provide a liquid cosmetic, which can be smoothly ejected without causing clogging in the liquid ejection path and prevents precipitation by increasing the viscosity without any loss of ejection performance, is excellent in water resistance and abrasion resistance, and can be closely adhered to the skin without letting the ejected high-brightness particles come off in flakes, even if the liquid cosmetic, suitable for eye makeup cosmetics for eyeliner around the eyes or eyebrows, includes high-brightness particles having large particle sizes to exert a glittering effect around eyes.

Particularly, as a tool for applying the liquid cosmetic of the present composition, a liquid applicator having an applying part filled with the liquid cosmetic can be used.

As an available liquid applicator having an applying part, any, not particularly limited, can be used as long as it is a container to be filled with the liquid cosmetic, having an applying part formed of a brush, pen tip, rubber, elastomer, or a closed cell type porous body having resiliency for eyeliner or eyebrow. However, use of a liquid applicator that can be filled with the liquid cosmetic inside its body and has a liquid thrusting mechanism by pressurizing is preferable.

Figure 1:
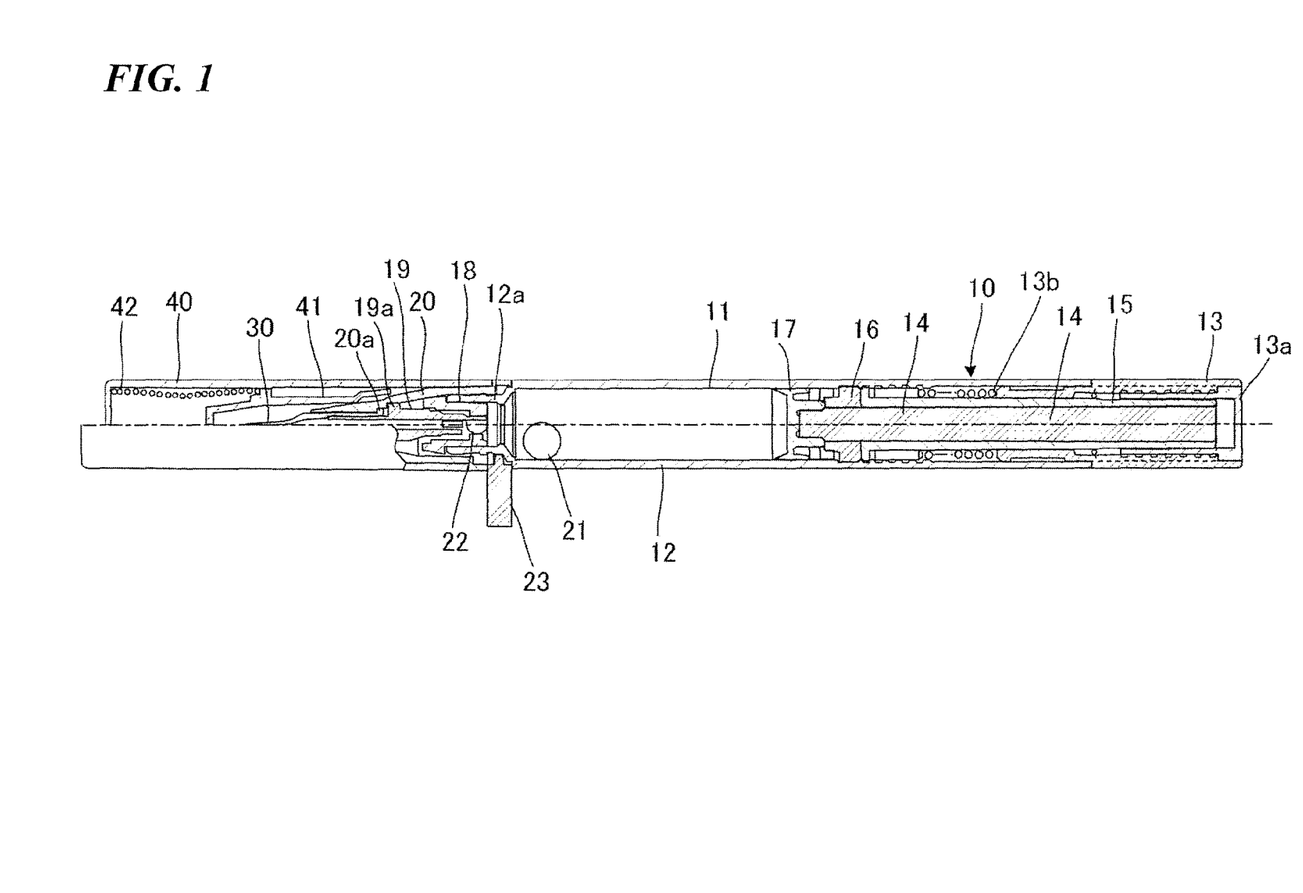
FIG. 1 is a whole sectional illustrative diagram showing one example of a liquid applicator filled with a liquid cosmetic of the present invention.

As an applicator efficiently filled with the liquid cosmetic of the present invention, use of a liquid applicator having a liquid thrusting mechanism of a rotary propelling dispensing type shown in FIG. 1 is preferable.

As shown in FIG. 1, the liquid applicator of this type includes an applying part 30 formed of thermosetting rubber or thermosetting elastomer, or thermoplastic rubber or thermoplastic elastomer, disposed in front of a cosmetic storing container to be a reservoir 11 for ejecting the liquid cosmetic of the present invention (which will be simply referred to hereinbelow as "liquid cosmetic") stored in front of a liquid thrusting mechanism 10, by means of liquid thrusting mechanism 10.

Liquid thrusting mechanism 10 is configured to feed and dispense the liquid cosmetic in container (reservoir) 11 to applying part 30 by rotating a feeding member 13 arranged at the rear end of a barrel body 12, in a circumferential direction relative to barrel body 12.

This liquid thrusting mechanism 10 of the applicator includes feeding member 13 rotatably fit at the rear end of barrel body 12, a drive sleeve 15 transmitting user's rotational force on a feeding member 13 to a screw rod 14, a screw part 16 fixed to barrel body 12 and mating with screw rod 14, screw rod 14 having a piston body 17 rotatably engaged at the front end thereof, and piston body 17 that slides inside reservoir 11 of barrel body 12. Rotation of feeding member 13 is transmitted to screw rod 14 by means of the drive sleeve 15. As this screw rod 14 rotates, the screw rod 14 and piston body 17 move forwards by means of female screw of nut-like screwed part 16 to feed the liquid cosmetic from reservoir 11 to applying part 30.

As shown in FIG. 1, feeding member 13 is a cylindrical actuator which is closed with a crown 13a fitted in at the rear end thereof and is rotatably fitted in the rear end part of barrel body 12 and partly exposed. Drive sleeve 15 is fitted inside feeding member 13 and fixed with respect to the rotational direction. Screwed part 16 is attached inside this drive sleeve 15 so as to be fixed in the rotational direction and relatively movable with respect to the axial direction (the screwed part does not move). Designated at 13b is a spring member, which urges feeding member 13 to be a rotary part rearwards (which urges a part called cam piece located under arrow 10 in FIG. 1 in the front direction).

In the present applicator, a sealing part 18, joint member 19, front barrel 20 and applying part 30 are assembled by fit-in to the front end part designated at 12a of barrel body 12. Reservoir 11 of barrel body 12 stores the liquid cosmetic. The liquid cosmetic delivered from the reservoir 11 passes through the flow passage inside joint member 19 to be ejected to applying part 30 so as to be applicable. Further, front barrel 20 is formed so that a cap 40 can be attached thereto (fitted thereon) to cover applying part 30 and front barrel 20 after use.

In FIG. 1, a reference numeral 21 in the drawing is an stirring ball that stirs the liquid cosmetic in reservoir 11 by its to-and-fro motion. Designated at 22 is a sealing ball. Designated at 41 and 42 are an inner cap inside cap 40 and a spring for urging the inner cap rearwards, respectively. Here, stirring ball 21 may be omitted.

Further, a reference numeral 23 in the drawing is a stopper, which, having an annular part inserted between the rear end of the front barrel 20 and the front side at the stepped portion of front end 12a of barrel body 12, positions sealing part 18, joint member 19, front barrel 20 and applying part 30 such as to shut off the flow passage of the liquid cosmetic toward applying part 30 when the applicator is not in use. The stopper 23 is integrally formed of an annular piece having a partial cutout and a grip piece arranged on the opposite side of the cutout, so that the annular part becomes greater in diameter with the expansion of the cutout part and can be disengaged from between the rear end of the front barrel 20 and front end part 12a of barrel body 12.

As shown in FIG. 1, when the applicator is not in use, sealing ball 22 fits in the bore of sealing part 18 to be the sealing ball socket and seals so that the liquid cosmetic will not flow into the applying part 30 side. On the other hand, when the applicator is in use, the user pulls out stopper 23 from barrel body 12 and pushes front barrel 20 toward the rear side, whereby the small-diametric portion at the rear end of joint member 19 abuts sealing ball 22. Then, the sealing ball 22 is dislodged from the bore of sealing part 18 to go into the reservoir 11, whereby the liquid cosmetic inside the reservoir 11 flows into the liquid flow passage of applying part 30 through the bore of joint member 19 and is supplied to applying part 30 from its interior so that the cosmetic can be applied to the target part.

Figure 2A:
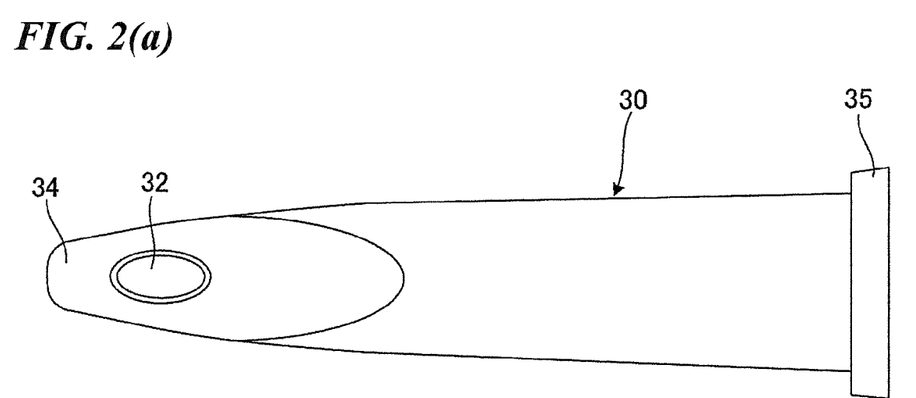
Figure 2B:
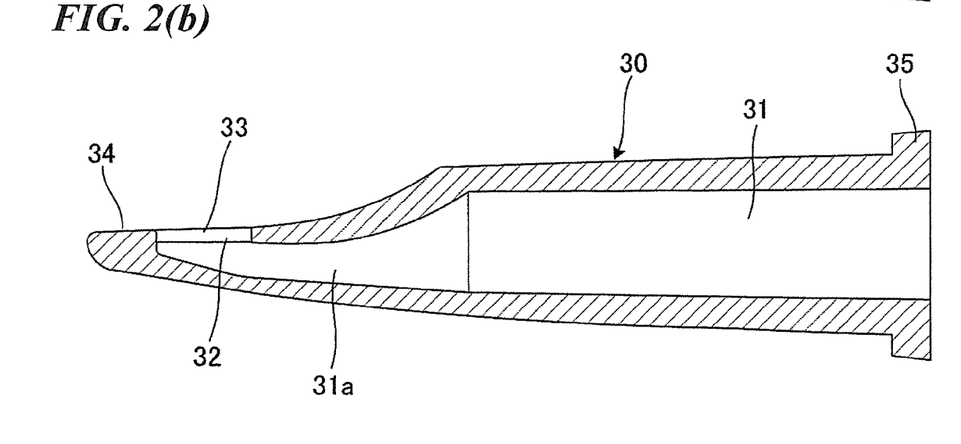

Applying part 30 to be the present invention has a tapered configuration as shown in FIGS. 2(a) and 2(b). The applying part 30 has a liquid flow passage 31 formed therein to be the liquid ejection path. Applying part 30 includes an applying face 34, which has a single liquid cosmetic delivery opening 32 (an oval opening in a plan view in the present embodiment) to communicate with liquid flow passage 31 inside applying part 30 while the face of opening 32 forms an approximately flat plane or inclined plane (an approximately flat plane in the present embodiment) 33, and which has a tapering approximate flat plane further extended forwards from the face of opening 32. The portion of the applying part except applying face 34 that has a tapering approximate flat plane further extended forwards from the face of opening 32, has a liquid flow passage 31a of a shape approximately similar to the external shape thereof. This applying part 30 is fitted into front barrel 20 and fixed with a rear flange part 35 held between a rear step 20a of front barrel 20 and front end part 19a of joint member 19.

Figure 3A:
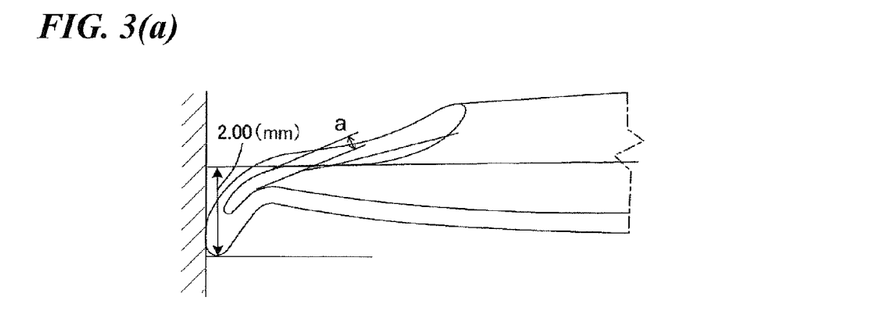
Figure 3B:
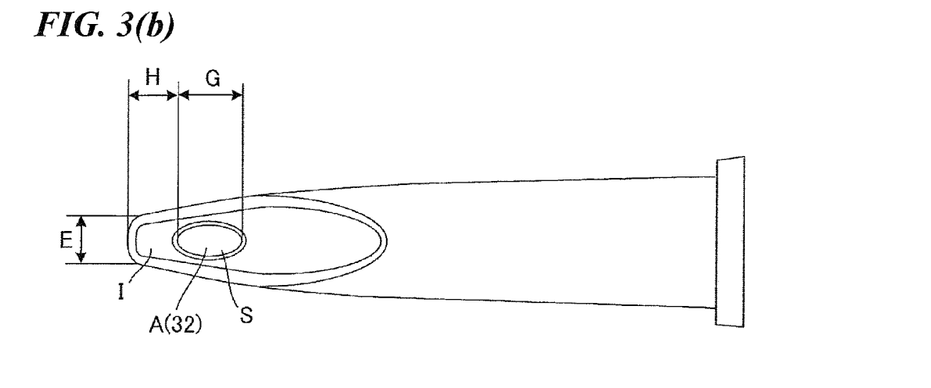
Figure 3C:
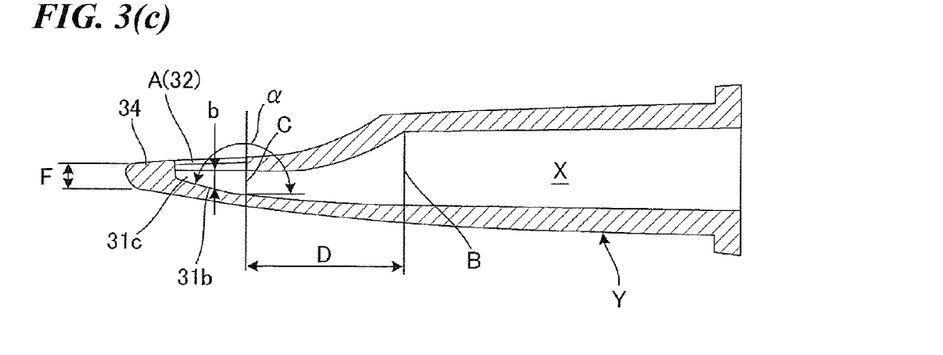

In this applying part 30, it is preferable to satisfy the following expression (I):

$$a/b < 0.9 \qquad (I),$$

where, as shown in FIGS. 3(a) to (c), a is the distance between opening A (designated at 32 in the drawing, the same hereinafter) and the liquid flow passage bottom 31b under opening A when the applying part is flexed 2 mm, setting the tip of applying face 34 that has tapering approximate flat plane I further extended forwards from the face of opening A, as a start point while b is the distance between opening A and the liquid flow passage bottom under opening A before flexing.

The above expression (I) is an expression representing the relationship of the distance at which liquid flow passage bottom 31b under opening A comes close to opening A when the applying part is flexed by setting the tip of applying face 34 that has tapering approximate flat plane I further extended forwards from the face of opening A, as a start point. It is more preferable if the relationship: $0.5 \leq a/b < 0.9$ is satisfied.

When the above expression (I) is satisfied, it is possible to prevent the liquid cosmetic from clogging up in flow passage 31a inside the applying part. In particular, the configuration can exert an effect in a long-term non-use.

Further detailing the technical meaning of the above expression (I), when the applying part is flexed by setting the distal end of applying face 34 that has tapering approximate flat plane I further extended forwards from the face of opening A, as an abutment (see FIG. 3(a)), the applying part forms a point of flexion around the portion under opening A so that the liquid flow passage bottom 31b under opening A comes close to the opening. More detailedly, a liquid flow passage 31c under opening A is preferably formed as an inclined plane from the bottom of the liquid cosmetic puddle under opening A in the direction of almost a tapering applying plane I, forming an angle (α) of 160° to 175°.

When this applicator is used, a flexion point is readily formed around the beginning of the inclined plane during application. By this effect, a flexion point occurs around the bottom of opening A, and liquid flow passage bottom 31b under opening A comes close to opening A so that the liquid cosmetic held in liquid flow passage 31c flows out from opening A to be additionally supplied to the initially formed hemispherical drop of the liquid cosmetic, thus making it possible to draw a longer application line.

Further, particularly when the liquid cosmetic contains large high-brightness particles of 150 μm to 500 μm of the present invention, if the bottom under opening A is liable to deform, the liquid flow passage bottom 31b under opening A comes close to opening A, so that it is possible to produce such effect as to reduce layering of large particles. Moreover, when the liquid cosmetic containing large particles is repeatedly applied on the area where the liquid cosmetic has been once applied, the liquid flow passage bottom 31b under opening A is located close to opening A, so that it is possible to prevent opening A from catching up the large particles thereinto.

Further, it is more preferable that, all the following expressions (II) to (IV) are satisfied as well as the above expression (I):

$$1.5 \text{ mm}^2 < B < 3.0 \text{ mm}^2 \qquad (II)$$

$$0.5 \text{ mm}^2 < C < B \qquad (III)$$

$$0.6 \text{ mm}^2 < S < 2.0 \text{ mm}^2 \qquad (IV)$$

where B is the area of cross section of the liquid flow passage inside applying part 30, C is the area of cross section of the liquid flow passage adjacent to opening A and S is the area of opening A, as shown in FIGS. 3(*b*) and 3(*c*).

Further, satisfaction of all the above expressions (II) to (IV) enables drawing of beautiful fine application lines, and also having a large internal space compared to the external size of the applying part. Formation of applying part 30 within these ranges secures the flow path and deformability efficiently, hence it is possible to further enhance the effect of the present invention.

In detail, if all the above expressions (II) to (IV) are satisfied, the liquid cosmetic ejected from opening A flows out approximately hemispherically. The hemispherical puddle of liquid cosmetic is moved from the tip of the applying face having the tapering approximately flat plane extended forwards from the opening face as the start point, toward the opening side. Then the hemispherical puddle of liquid cosmetic moves to applying face 34 that has tapering approximate flat plane I further extended forwards from the face of opening A, with a necessary and sufficient amount. As a result, a beautiful fine application line can be drawn. Further, the start point of drawing an application line corresponds to the tip of tapering approximate flat plane I further extended forwards from the face of opening A, so that the beginning of an application line is made easy to draw. Moreover, provision such as grooves on tapering approximately flat plane I in the fore part of the face of opening A makes more preferable effect.

Still more, the aforementioned effect of liquid flow passage bottom 31*b* under opening A being moved close to opening A may be obtained. If the ratio between the length H of the applying face arranged in front of the face of opening A and the major axis G of the opening falls out of the preferable range, i.e., 0.7<(H/G)<1.6 as in the related art, only the applying face located in front of the face of opening A flexes without producing any effect of letting liquid flow passage bottom 31*b* under opening A move close to opening A. In such a case, the liquid cosmetic for forming an application liquid line runs out, so that it is necessary to perform an operation of flowing out the liquid cosmetic from opening A once again, resulting in annoying in the wide area application. Further, because the aforementioned effect of causing liquid flow passage bottom 31*b* under opening A to come close to opening A is lost, when the liquid cosmetic contains large particles, the large particles are liable to layer on opening A, which causes the applicator faults in repeating use. Satisfaction of all the above expressions (II) to (IV) can solve such all problems.

For simply achieving ejection, the problem of the supply amount of the liquid cosmetic and the problem of layering of large particles when the liquid cosmetic contains large particles, can be avoided by setting the amount of liquid to increase and designing the size of opening A to expand. However, problems such as failure to draw an application line, adherence of too much amount of liquid, and missing of the start point of the application line, occurrence of trouble due to blocking of view by the applicator when makeup is done by viewing a mirror.

Satisfaction of all the above expressions (II) to (IV) can solve also such problems. Further more, by setting the length H of the applying face to be thin (thickness F of the applying face is set at 0.5 to 1.2 mm, for instance), the distance for the applying face forwards from the opening A becomes short and it is possible to provide a structure that readily produces the flexion point around the bottom of the opening, whereby the area under the liquid flow passage in the vicinity of cross section C can be deformed easily and the liquid can be readily dispensed.

In thus configured liquid applicator, it is also preferable that, as to the ratio of the sum of B representing the area of the cross section of the liquid flow passage and C representing the area of the cross section of the liquid flow passage, divided by D representing the distance of the liquid flow passage B to C, the following expression (V) holds (see FIG. 3(*c*)):—

$$(B+C)/D > 0.5 \text{ mm} \qquad (V).$$

Further, it is preferably that the ratio between the external volume Y of the section of the dispensing part from front barrel 20 except applying face 34 that has tapering approximate flat plane I further extended forwards from the face of opening A, and the volume X of the liquid flow passage having an approximately similar shape, satisfies the following expression (VI) (see FIG. 3(*c*)):—

$$X/Y > 0.4 \qquad (VI).$$

Satisfaction of the above expression (V) and/or expression (VI) makes it possible to secure a larger internal space compared to the external shape of the applying part. Forming applying part 30 specified in the above ranges (the above expression (V) and/or expression (VI), or the above expression (V) and/or expression (VI) further including the above expressions (II) to (IV)) secures further the flow passage and deformability effectively in a synergy manner, hence, thus enabling efficient application of the liquid cosmetic of the present invention.

Applying part 30 having the structural characteristics described above can be integrally formed with thermosetting rubber or thermosetting elastomer such as silicone rubber, urethane rubber, acrylic rubber, ethylene propylene diene rubber, ethylene propylene rubber, butyl rubber, nitrile rubber, isoprene rubber, butadiene rubber, fluoro rubber, and epichrolhydrine rubber, preferably thermosetting rubber or thermosetting elastomer having a durometer A hardness of 10 to 70.

It is also possible to integrally form applying part 30 with a material such as thermoplastic rubber, thermoplastic elastomer of styrenes, esters, and urethanes. When materials such as thermoplastic rubber, and thermoplastic elastomer are used, use of styrene elastomers is preferable in view of formability, applying performance, usability and the like. Moreover, in order to improve applying performance and operability, when the hardness of the applying body is too low, the aforementioned thermoplastic elastomer blended with a resin such as PP, PE, TPU and PBT, may be used so that the durometer A hardness becomes 70 or higher.

As a more preferable applying part, in view of moldability, applying performance, usability and others, fluid silicone rubber may be used to integrally form an applying part by the LIM molding technique (a molding technique called Liquid Injection Molding) or styrene elastomer may be used to perform integrally molding.

Further, in applying part 30 that satisfies at least one of the above expressions (I), (II) to (IV) and (V), it is preferable that the distance D from liquid flow passage B inside the applying part to the liquid flow passage C adjacent to opening A is specified to satisfy 0 mm<D<5 mm while the tip of the applying face that has tapering approximate flat plane/further extended forwards from the face of opening A is formed so that the width E of the tip in the opening face view satisfy 0.8 mm<E<1.6 mm.

In the present liquid applicator of the embodiment shown in FIGS. 1 to 3 (including FIG. 4 below), the values in expressions (I) to (V) are as follows:—

'a', the distance to the liquid flow passage bottom 31*b* under opening A: 0.16 mm, 'b', the distance between opening A and the liquid flow passage bottom under opening A before flexing: 0.37 mm, a/b=0.43, 'B', the area of the cross-section of the liquid flow passage inside applying part 30: 2.54 mm$^2$, 'C', the area of the cross-section of the liquid flow passage adjacent to opening A: 0.74 mm$^2$, 'S', the area of opening A: 0.94 mm$^2$, (B+C)/D=0.86 mm, 'Y', the external volume: 14.4 mm$^3$, 'X', the volume of the liquid flow passage: 9 mm$^3$, X/Y=0.63.

Also, the values in FIGS. 3(*b*) and 3(*c*) were set such that H=1.2 mm, G=1.6 mm, H/G=0.75, D=3.8 mm, E=1.2 mm, F=0.7 mm, angle ($\alpha$)=170°. The applying part 30 having such structural characteristics was formed by the LIM forming technique using fluid silicone rubber (KE1940, manufactured by Shin'Etsu Chemical Co., Ltd.).

In accordance with the liquid applicator of the present embodiment, it is possible to smoothly eject the liquid cosmetic of the present invention and hold a small amount of the liquid cosmetic such as a makeup cosmetic in the liquid cosmetic flow-out opening and make the applying part small and the width of the applying face disposed in front of the liquid cosmetic flow-out opening small even for a tapering applying face and external dimensions, without causing clogging inside the applying part. As a result, it is possible to easily draw fine application lines.

Particularly, when applying part 30 is flexed 2 mm from the tip of applying face 34 that has tapering approximate flat plane/further extended forwards from the face of opening 32, as the start point, in the applying part that satisfies the above expression (I), the applying part forms a point of flexion around the portion under the opening so that the liquid flow passage bottom under the opening comes close to the opening if the applying part is flexed by setting the tip of the applying face that has tapering approximate flat plane further extended forwards from the opening face, as a supporting point. As a result, during the application, a flexion point is prone to form around the beginning of the inclination. Due to this effect, a flexion point is formed around the area under opening A, whereby the cosmetic held in the liquid flow passage flows out from opening to be additionally supplied to the initially formed hemispherical drop of the liquid cosmetic, thus making it possible to draw a longer application line. When the liquid cosmetic contains large high-brightness particles, the bottom under opening A is liable to deform, or the liquid flow passage bottom under opening A comes close to opening A, so that it is possible to produce such effect as to reduce the layering of large particles. Moreover, when the liquid cosmetic containing large particles is repeatedly applied on the area where the liquid cosmetic has been once applied, the liquid flow passage bottom 31*b* under opening A is located close to opening A, so that it is possible to prevent large particles from layering around opening A.

The liquid applicator of the above configuration has been described taking an example of a liquid applicator for liquid eyeliner and liquid eyeshadow. However, the liquid applicator should not be limited to this, and can also be applied to eyebrow applicators for drawing lines on eyebrows, and for drawing lines on the skin.

Further, the edges of peripheral surface of opening 32 and applying face 34 of applying part 30 may be beveled.

Further, as the liquid thrusting mechanism for the above liquid applicator, the applicator of a rotary propelling dispensing type shown in FIG. 1 is used. However, for example, an applicator of a click-dispensing type shown in FIG. 4 may be used.

Figure 4:
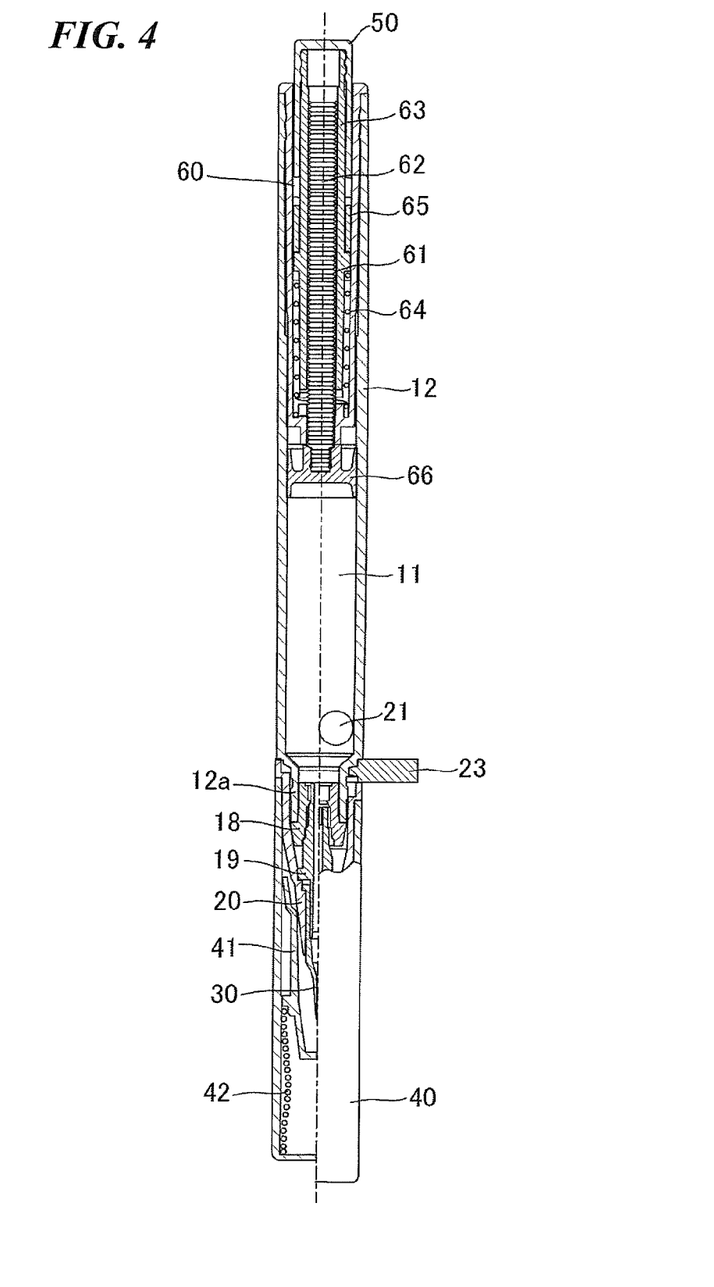
FIG. 4 is a whole sectional illustrative diagram of a liquid applicator using another type of liquid thrusting mechanism for a liquid applicator of the present invention.

FIG. 4 is an illustrative diagram of a click dispensing type liquid applicator. Here, in FIG. 4, the same parts as in the above configuration are assigned with the same reference numerals without description.

The applicator of a click-dispensing type according to this embodiment can dispense a liquid cosmetic in reservoir 11 by pushing a click member 50 arranged at the rear end of barrel body 12 forwards in the axial direction as shown in FIG. 4, includes: a clicking device 60 for converting the pushing force of user's clicking on click member 40 into a screwed body 61 fixed to barrel body 12; and a screw rod 62 mated with screwed body 61, and is constructed such that screw rod 62 is rotated by the rotational force converted by the clicking device 60 and moved forwards through screwed body 61 to thereby dispense the liquid cosmetic. The clicking device 60 for converting the pushing force on clicking member 50 essentially composed of a rotary part 63 having first and second cam surfaces, screwed body 61 having a first fixed cam surface and a cam body 65 having a second fixed cam surface.

In the present click dispensing type liquid applicator, as a click is started by pushing clicking member 50 in the axial direction, clicking member 40 and rotary part 63 integrally move forwards as compressing a spring member 64. As clicking is further continued, rotary part 63 moves forwards whilst it is rotating in a predetermined direction. During the action, since rotary part 63 is rotatably attached to clicking member 50, clicking member 50 itself does not rotate. With the rotation of rotary part 63 during clicking, screw rod 62 which is restricted to rotate relative to rotary part 63 and freely moves in the axial direction, rotates together with rotary part 63. Screw rod 62 moves forwards together with a piston body 66 by the function of screw engagement with screwed body 61 to thereby dispense the liquid cosmetic in reservoir 11. From the state, clicking is released. Spring member 64 disposed inside screw body 61 pushes up rotary body 63 to thereby release clicking. At the point, rotary body 63 starts rotating in the predetermined rotational direction and moving backwards. As release of clicking is continued, the push-up force of spring member 64 moves rotary body 63 backward whilst it is also rotating. Also during the rotation, the rotary body rotates screw rod 62 and moves forwards together with piston body 66 to thereby dispense the liquid cosmetic as mentioned above. When the above mentioned clicking action is repeated, the clicking action and releasing action in the axial direction are converted to rotational force so as to rotate screw rod 62, whereby piston body 66 can be pushed forwards to dispense a predetermined amount of liquid cosmetic.

Figure 5:
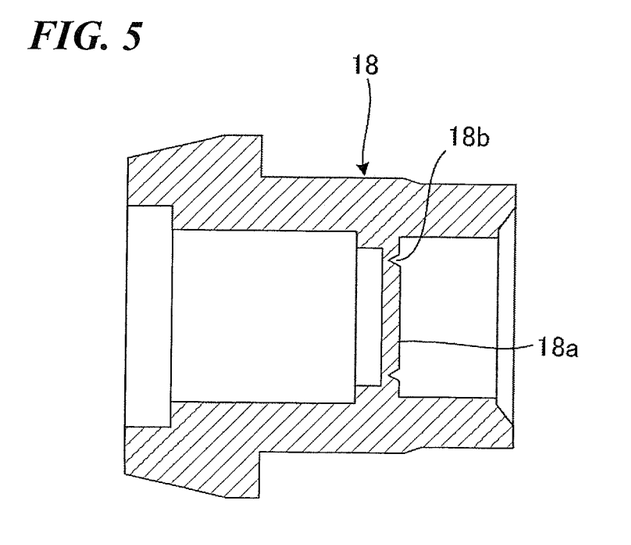
FIG. 5 is a whole sectional illustrative diagram of a sealing part using another type of sealing part for a liquid applicator of the present invention.

Further, in the liquid applicator of the configuration shown in FIG. 1 and others, in order to seal joint member 19, sealing ball 22 is used in combination with seal 18 as a sealing ball socket. However, the present invention should not be limited to use of sealing ball 22. For example, as shown in FIG. 5, it is possible to provide an annular thin film 18*a* as a sealing member, integrally inside sealing part 18 as shown in FIG. 5, and use it in place of sealing ball 22.

In this configuration, when the applicator is not in use, annular thin film 18a seals the liquid flow passage inside sealing part 18 so that the liquid cosmetic will not flow into the applying part 30 side. On the other hand, when the applicator is in use, the user pulls out stopper 23 from barrel body 12 and pushes front barrel 20 toward the rear side similarly to the above first embodiment, whereby the small-diametric portion at the rear end of joint member 19 abuts annular thin film 18a so that annular thin film 18a is dislodged in part from the bore of sealing ball socket 18 by the function of a cutout groove (V-shaped groove in section) formed along the circumference of annular thin film 18a. As a result, the liquid cosmetic inside the reservoir 11 flows into the liquid flow passage of applying part 30 through the bore of joint member 19 and is supplied to applying part 30 from its interior so that the cosmetic can be applied to the target part.

EXAMPLES

Next, the present invention will be further detailedly explained referring to examples and comparative examples, however, the present invention should not be limited to the following examples and others.

Examples 1-7 and Comparative Examples 1-4

The liquid cosmetics were prepared based on the blending prescriptions shown in the following Tables 1 and 2 (blending unit: % by mass, the total amount 100% by mass). These components were mixed by stirring for three hours at room temperature. As a result, the liquid cosmetics shown in each Table were obtained.

For each liquid cosmetic thus obtained, the viscosity was measured by the following method while water resistance and abrasion resistance, condition of pigment precipitation, clogging and ejection performance of the applying part were evaluated.

(Viscosity Measurement Method)

For the thus obtained liquid cosmetics, the viscosities at a shear rate of 3.83 s$^{-1}$, 19.20 s$^{-1}$, 38.3 s$^{-1}$ and 76.8 s$^{-1}$, were measured by an EMD type viscometer at 25° C. using a standard cone rotor with a speed of 20 rpm.

(Evaluation Method of Water Resistance and Abrasion Resistance)

As for water resistance and abrasion resistance, the liquid cosmetic was applied on the back of the hand, and naturally dried for 10 minutes, then the applied area was rinsed with running and rubbed with a finger. The extent to which the applied material came off was visually observed and the feeling of the finger was sensually evaluated based on the following evaluation criteria.

○: The applied part did not peel off, presented good result.
Δ: The applied part peeled off in part.
X: Most of the applied part peeled off.

(Evaluation Method of Condition of Pigment Precipitation)

Liquid applicators (the loaded amount of liquid cosmetic: 1.4 ml) conforming to that shown in FIG. 1 had been left at 50° C. with the top side down for three months. The condition of pigment precipitation was visually observed, and evaluated based on the following criteria:—

○: No pigment precipitation was found.
Δ: Light pigment precipitation occurred, and a top clear layer of less than 2 mm developed.
X: Pigment precipitation occurred, and a top clear layer of 2 mm or more developed.

(Evaluation Method of Clogging and Ejection Performance of Applying Part)

Liquid applicators (the loaded amount of liquid cosmetic: 1.4 ml) conforming to that shown in FIG. 1 had been left at 25° C. without a cap for three days, so that the ejection performance of the liquid content was evaluated based on the following criteria:—

○: The content liquid did not clog in the liquid ejection flow passage, and could be ejected normally.
Δ: No clog occurred but uneven application took place.
X: The content liquid clogged in the liquid ejection flow passage and could not be applied.

TABLE 1

| | | | | | | (Total Amount 100% by mass) | | |
|---|---|---|---|---|---|---|---|---|
| | | Example 1 | Example 2 | Example 3 | Example 4 | Example 5 | Example 6 | Example 7 |
| Coloring Material (High-brightness Particles) | Polyethylene Terephthalate • Polymethyl Methacrylate Laminate Film Powder *1 | 4 | 0 | 4 | 0 | 4 | 0 | 5 |
| | Polyethylene Terephthalate • Polymethyl Methacrylate Laminate Film Powder *2 | 0 | 4 | 0 | 0 | 0 | 4 | 0 |
| | Red ochre-coated Mica-titanium *3 | 0 | 0 | 0 | 5 | 0 | 0 | 0 |
| Coating Film Forming Resin | Alkyl Acrylate Copolymer *4 | 4 | 4 | 3 | 8 | 4 | 4 | 4 |
| Anionic Polymer Compound 1 | Methylvinyl Ether/Maleic Acid Crosspolymer *5 | 0.4 | 1 | 1 | 1 | 0 | 0 | 0 |
| Anionic Polymer Compound 2 | Acrylates/C10-30 Alkyl Acrylate Crosspolymer *6 | 0 | 0 | 0 | 0 | 0.5 | 1 | 0 |
| Anionic Polymer Compound 3 | Acrylic Acid/Vinylpyrrolidone Crosspolymer *7 | 0 | 0 | 0 | 0 | 0 | 0 | 1 |
| pH Modifier | Aminomethyl Propanol | 0.3 | 0.6 | 0.6 | 0.6 | 0.25 | 0.5 | 0.9 |
| Chelating Agent | Disodium Ethylendiaminetetraacaetate | 0.3 | 0.3 | 0.3 | 0.3 | 0.3 | 0.3 | 0.3 |
| Moisturizing Agent | 1,3-Butylene Glycol | 10 | 10 | 10 | 10 | 10 | 10 | 10 |
| Preservative | Phenoxyethanol | 0.4 | 0.4 | 0.4 | 0.4 | 0.4 | 0.4 | 0.4 |
| Preservative | Methyl Paraben | 0.3 | 0.3 | 0.3 | 0.3 | 0.3 | 0.3 | 0.3 |
| Preservative | Sodium Dehydroacetate | 0.1 | 0.1 | 0.1 | 0.1 | 0.1 | 0.1 | 0.1 |
| Water | Purified Water | Balance | Balance | Balance | Balance | Balance | Balance | Balance |

TABLE 1-continued

|  |  | Example 1 | Example 2 | Example 3 | Example 4 | Example 5 | Example 6 | Example 7 |
|---|---|---|---|---|---|---|---|---|
| Performance Evaluation Results |  |  |  |  |  |  |  |  |
| Viscosity (mPa·s) *8 | Shear Rate 3.83 s$^{-1}$ | 3588 | 6670 | 7425 | 8480 | 3650 | 3980 | 6248 |
|  | Shear Rate 19.2 s$^{-1}$ | 1118 | 1860 | 1900 | 2170 | 1134 | 1450 | 1742 |
|  | Shear Rate 38.3 s$^{-1}$ | 641 | 1072 | 913 | 1043 | 649 | 949 | 1004 |
|  | Shear Rate 76.8 s$^{-1}$ | 289 | 664 | 598 | 683 | 294 | 621 | 622 |
| Water Resistance• Abrasion Resistance |  | ○ | ○ | ○ | ○ | ○ | ○ | ○ |
| Condition of Pigment Precipitation |  | ○ | ○ | ○ | ○ | ○ | ○ | ○ |
| Applying Performance |  | ○ | ○ | ○ | ○ | ○ | ○ | Δ |

*1 Particle Size 200 μm
*2 Particle Size 150 μm
*3 Particle Size 70 μm
*4 Alkyl Acrylate Copolymer •••Luvimer 100P (manufactured by BASF SE)
*5 Methylvinyl Ether/Maleic Acid Crosspolymer ••• STABILEZE (manufactured by ISP Inc.)
*6 Acrylates/C10-30 Alkyl Acrylate Crosspolymer •••Carbopol (manufactured by BF Goodrich Co.)
*7 Acrylic Acid/Vinylpyrrolidone Crosspolymer ••• Ultra Thix P-100 (manufactured by ISP Inc.)
*8 Viscosity Measurement Condition: EMD type Viscometer (manufactured by TOKI SANGYO CO., LTD. Standard Corn Rotor: 20 rpm for each shear rate

TABLE 2

|  |  | Comparative Example 1 | Comparative Example 2 | Comparative Example 3 | Comparative Example 4 |
|---|---|---|---|---|---|
| Coloring Material (High-brightness Particles) | Polyethylene Terephthalate•Polymethyl Methacrylate Laminate Film Powder *1 | 5 | 0 | 0 | 21 |
|  | Titanium oxide coated-glass Powder *2 | 0 | 10 | 0 | 0 |
|  | Red ochre-coated Mica-titanium *3 | 0 | 0 | 5 | 0 |
| Coating Film Forming Resin | Alkyl Acrylate Copolymer *4 | 4 | 4 | 1 | 1 |
| Anionic Polymer Compound 1 | Methylvinyl Ether/Maleic Acid Crosspolymer *5 | 0.2 | 3 | 1 | 1 |
| pH Modifier | Aminomethyl Propanol | 0.12 | 1.8 | 0.6 | 0.6 |
| Chelating Agent | Disodium ethylendiaminetetraacetate | 0.3 | 0.3 | 0.3 | 0.3 |
| Moisturizing Agent | 1,3-Butylene Glycol | 10 | 10 | 10 | 10 |
| Preservative | Phenoxyethanol | 0.4 | 0.4 | 0.4 | 0.4 |
| Preservative | Methyl Paraben | 0.3 | 0.3 | 0.3 | 0.3 |
| Preservative | Sodium Dehydroacetate | 0.1 | 0.1 | 0.1 | 0.1 |
| Water | Purified Water | Balance | Balance | Balance | Balance |
| Performance Evaluation Results |  |  |  |  |  |
| Viscosity (mPa·s)*8 | Shear Rate 3.83 s$^{-1}$ | 2719 | 55375 | 6667 | 9696 |
|  | Shear Rate 19.2 s$^{-1}$ | 696 | 14170 | 1706 | 2481 |
|  | Shear Rate 38.3 s$^{-1}$ | 334 | 6811 | 820 | 1192 |
|  | Shear Rate 76.8 s$^{-1}$ | 219 | 4460 | 537 | 781 |
| Water Resistance•Abrasion Resistance |  | ○ | ○ | X | ○ |
| Condition of Pigment Precipitation |  | X | ○ | ○ | ○ |
| Applying Performance |  | X | X | Δ | X |

*1: Particle Size 200 μm
*2: Particle Size 150 μm
*3: Particle Size 70 μm
*4: Alkyl Acrylate Copolyme•••Luvimer 100P (manufactured by BASF SE.)
*5: Methylvinyl Ether/Maleic Acid Crosspolymer•••STABILEZE (manufactured by ISP Inc.)
*8 Viscosity Measurement Condition: EMD type Viscometer (manufactured by TOKI SANGYO CO., LTD. Standard Corn Rotor: 20 rpm for each shear rate As apparent from the results in the above Table 1 and Table 2, it was found that the liquid cosmetics of examples 1 to 7 within the scope of the present invention are more excellent in water resistance, water abrasion, condition of pigment precipitation, application performance (clogging in the applying part), compared to comparative examples 1 to 4, which are out of the scope of the present invention.

It is possible to provide eye-makeup cosmetics suitable for eye-liner and eye brows.

LETTERS AND NUMERALS

10 liquid thrusting mechanism
12 barrel body
13 feeding member
17 piston body,
18 sealing part
19 joint member
20 front barrel
30 applying part
31 liquid flow passage
32 opening
34 applying face

The invention claimed is:
1. A liquid cosmetic comprising, at least, 1 to 20% by mass of high-brightness particles, 2 to 10% by mass of film-forming resin, 0.3 to 2% by mass of an anionic polymer compound having a thickening effect, and water, wherein the viscosity at 25° C. and a shear rate of 76.8 s$^{-1}$ in an EMD type viscometer falls within the range of 250 to 1,000 mPa·s.

2. The liquid cosmetic described in claim 1, wherein the anionic polymer compound having a thickening effect includes, at least, one kind of crosspolymers selected from a group consisting of methylvinyl ether/maleic acid crosspolymer, acrylates/acrylate ester of alkyl having 10 to 30 carbon atoms crosspolymer, and acrylic acid/vinylpyrrolidone crosspolymer.

3. The liquid cosmetic described in claim 1, which is used as an eye makeup cosmetic.

4. The liquid cosmetic described in claim 1, wherein the color of the vehicle (base) is transparent.

5. The liquid cosmetic described in claim 1, which is stored in a liquid applicator having an applying part.

* * * * *